(12) United States Patent
Gresser et al.

(10) Patent No.: US 7,077,866 B2
(45) Date of Patent: Jul. 18, 2006

(54) RESORBABLE INTERBODY SPINAL FUSION DEVICES

(75) Inventors: Joseph D. Gresser, Brookline, MA (US); Debra J. Trantolo, Princeton, MA (US); Robert S. Langer, Newton, MA (US); Kai-Uwe Lewandrowski, Brookline, MA (US); Alexander M. Klibanov, Newton, MA (US); Donald L. Wise, Belmont, MA (US)

(73) Assignee: DePuy Mitek, Inc., Norwood, MA (US)

( * ) Notice: Subject to any disclaimer, the term of this patent is extended or adjusted under 35 U.S.C. 154(b) by 0 days.

(21) Appl. No.: 09/785,593

(22) Filed: Feb. 16, 2001

(65) Prior Publication Data

US 2001/0008980 A1 Jul. 19, 2001

Related U.S. Application Data

(63) Continuation of application No. 09/131,716, filed on Aug. 10, 1998, now Pat. No. 6,241,771.

(60) Provisional application No. 60/055,291, filed on Aug. 13, 1997, provisional application No. 60/074,076, filed on Feb. 9, 1998, provisional application No. 60/074,197, filed on Feb. 10, 1998, provisional application No. 60/081,803, filed on Apr. 15, 1998.

(51) Int. Cl.
*A61F 2/44* (2006.01)

(52) U.S. Cl. ............... 623/17.16; 623/17.11; 623/23.75

(58) Field of Classification Search ............. 623/17.16, 623/23.58, 23.59, 23.71, 23.75, 926, 17.11; 606/65, 77

See application file for complete search history.

(56) References Cited

U.S. PATENT DOCUMENTS

| | | | |
|---|---|---|---|
| 3,867,728 A | 2/1975 | Stubstad et al. | 3/1 |
| 4,279,249 A | 7/1981 | Vert et al. | 128/92 |
| 4,349,921 A | 9/1982 | Kuntz | 3/1 |
| 4,492,226 A | 1/1985 | Belykh et al. | 128/92 |
| 4,501,269 A | 2/1985 | Bagby | 128/92 |
| 4,655,777 A | 4/1987 | Dunn et al. | 623/16 |
| 4,743,256 A | 5/1988 | Brantigan | 623/17 |
| 4,834,757 A | 5/1989 | Brantigan | 623/17 |

(Continued)

FOREIGN PATENT DOCUMENTS

WO  WO 9818408 A1 * 5/1998

*Primary Examiner*—Paul B. Prebilic
(74) *Attorney, Agent, or Firm*—Pabst Patent Group LLP

(57) ABSTRACT

A resorbable interbody fusion device for use in spinal fixation is disclosed. The device is composed of 25–100% bioresorbable or resorbable material. The interbody fusion device of the invention can be in any convenient form, such as a wedge, screw or cage. Preferably, the resorbable device of the invention is in the shape of a tapered wedge or cone, which further desirably incorporates structural features such as serrations or threads better to anchor the device in the adjoining vertebrae. The preferred device further comprises a plurality of peripheral voids and more desirably a central void space therein, which may desirably be filled with a grafting material for facilitating bony development and/or spinal fusion, such as an autologous grafting material. As the preferred material from which the resorbable interbody fusion device is manufactured is most likely to be a polymer that can produce acidic products upon hydrolytic degradation, the device preferably further includes a neutralization compound, or buffer, in sufficiently high concentration to decrease the rate of pH change as the device degrades, in order to prevent sterile abscess formation caused by the accumulation of unbuffered acidic products in the area of the implant.

24 Claims, 10 Drawing Sheets

U.S. PATENT DOCUMENTS

| | | | |
|---|---|---|---|
| 4,904,260 A | 2/1990 | Ray et al. | 623/17 |
| 4,961,740 A | 10/1990 | Ray et al. | 606/86 |
| 4,968,317 A | 11/1990 | Tormala et al. | 606/77 |
| 5,015,247 A | 5/1991 | Michelson | 606/61 |
| 5,026,373 A | 6/1991 | Ray et al. | 606/61 |
| 5,055,104 A | 10/1991 | Ray | 606/61 |
| 5,062,850 A | 11/1991 | MacMillan et al. | 623/17 |
| 5,171,278 A | 12/1992 | Pisharodi | 623/17 |
| 5,192,327 A | 3/1993 | Brantigan | 623/17 |
| D337,527 S | 7/1993 | Klapwald | D9/558 |
| 5,225,129 A * | 7/1993 | van den Berg | 264/85 |
| 5,246,458 A | 9/1993 | Graham | 623/17 |
| 5,306,309 A | 4/1994 | Wagner et al. | 623/17 |
| 5,397,364 A | 3/1995 | Kozak et al. | 623/17 |
| 5,443,514 A | 8/1995 | Steffee | 623/17 |
| 5,458,638 A | 10/1995 | Kuslich et al. | 623/17 |
| 5,489,307 A | 2/1996 | Kuslich et al. | 623/17 |
| 5,489,308 A | 2/1996 | Kuslich et al. | 623/17 |
| 5,522,895 A | 6/1996 | Mikos | 623/16 |
| 5,522,899 A | 6/1996 | Michelson | 623/17 |
| 5,527,864 A | 6/1996 | Suggs et al. | 525/444 |
| 5,531,746 A | 7/1996 | Errico et al. | 606/61 |
| 5,545,229 A | 8/1996 | Parsons et al. | 623/17 |
| D377,095 S | 12/1996 | Michelson | D24/155 |
| D377,096 S | 12/1996 | Michelson | D24/155 |
| 5,593,409 A | 1/1997 | Michelson | 606/61 |
| 5,607,426 A | 3/1997 | Ralph et al. | 606/61 |
| 5,609,636 A | 3/1997 | Kohrs et al. | 623/17 |
| 5,645,598 A | 7/1997 | Brosnahan, III | 623/17 |
| 5,665,122 A | 9/1997 | Kambin | 623/17 |
| 5,683,465 A | 11/1997 | Shinn et al. | 623/17 |
| 5,702,455 A | 12/1997 | Saggar | 623/17 |
| 5,741,329 A * | 4/1998 | Agrawal et al. | 424/423 |
| 5,776,193 A * | 7/1998 | Kwan et al. | 424/423 |
| 5,817,328 A * | 10/1998 | Gresser et al. | 424/426 |
| 5,964,807 A | 10/1999 | Gan et al. | 623/17 |
| 5,989,289 A | 11/1999 | Coates et al. | 623/17 |
| 6,126,688 A | 10/2000 | McDonnell | 623/17.16 |
| 6,153,664 A * | 11/2000 | Wise et al. | 523/115 |
| 6,241,771 B1 * | 6/2001 | Gresser et al. | 623/17.16 |
| 6,419,945 B1 * | 7/2002 | Gresser et al. | 424/426 |

* cited by examiner

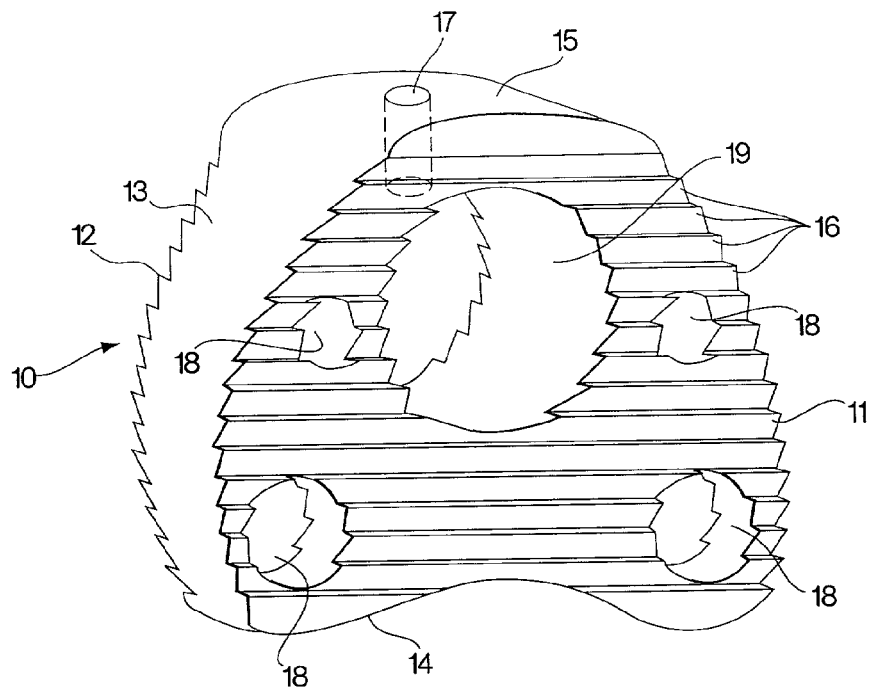
Fig. 1A
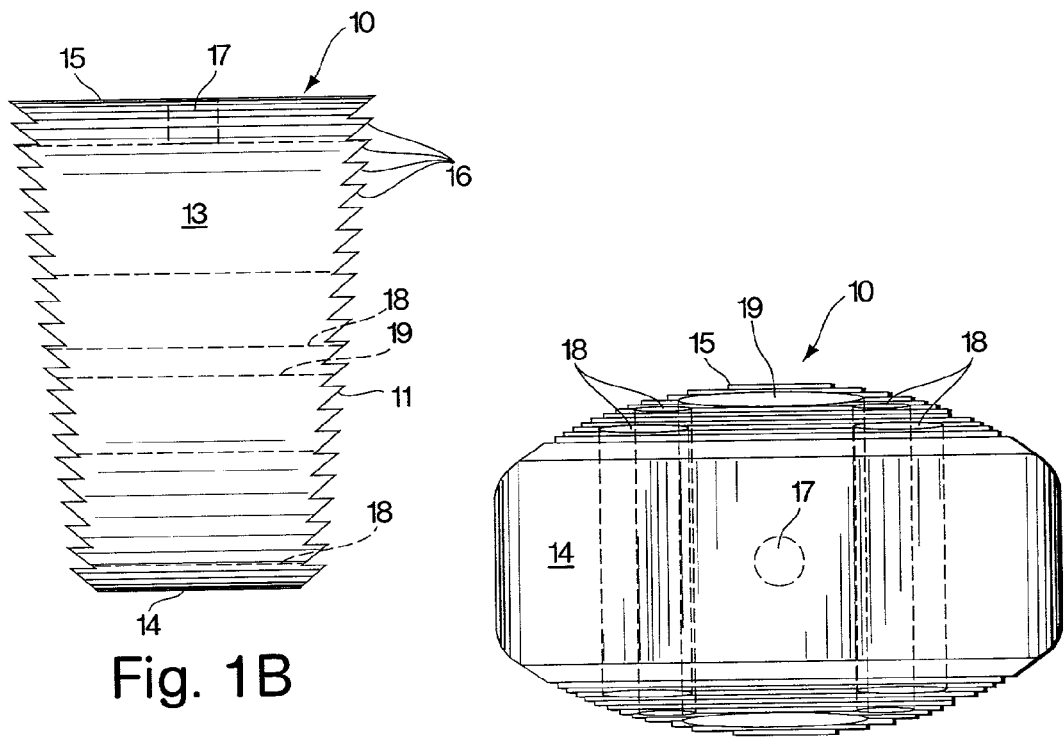
Fig. 1B
Fig. 1C

RESORBABLE INTERBODY SPINAL FUSION DEVICES

CROSS REFERENCE TO RELATED APPLICATIONS

This application is a continuation application of U.S. patent application Ser. No. 09/131,716, filed Aug. 10, 1998 (now U.S. Pat. No. 6,241,771), which claims priority to U.S. Provisional Application Nos. 60/055,291, filed Aug. 13, 1997; 60/074,076, filed Feb. 9, 1998; 60/074,197, filed Feb. 10, 1998, and 60/081,803, filed Apr. 15, 1998, the entire disclosures of which are incorporated herein by reference.

STATEMENT REGARDING FEDERALLY SPONSORED RESEARCH OR DEVELOPMENT

Not applicable

BACKGROUND OF THE INVENTION

The present invention relates to the field of interbody spinal fusion devices.

In the structure of the spine of vertebrates including humans, the space between adjacent vertebrae is referred to as the interbody space. In normal spines, this space is occupied by the structure commonly referred to as a disc. This intervertebral structure separates and cushions the vertebrae.

Various pathologic and traumatic conditions require excision of a spinal disc and stabilization of the superior and inferior vertebrae while bony fusion develops. In 1995, approximately 225,000 new spinal fusions were performed in the United States alone, and of these about one half were performed in the thoracic and cervical spine, with the remaining spinal fusions focused on the lumbar spine. To stabilize the spine where the surgery has occurred, an internal fixation device is frequently used. Such implants provide the ability to improve spinal alignment and maintain the developing alignment while fusion develops. Fixation of the spine can further correct deformity and provide immediate stability, thereby facilitating spinal fusion, early mobilization, and, when necessary, entry into rehabilitative programs.

The use of fixation devices is beneficial in several ways. First, the avoidance of long-term bed rest, thought by many to decrease non-neurological morbidity, is achieved. Additionally, fixation devices are thought to promote fracture healing and therefore reduce the need for rigid and cumbersome post-operative bracing.

While a number of commercially available implants for spinal stabilization are known, these devices are not resorbable and therefore, remain permanently at the implant site. Meticulous bone preparation and grafting is essential for successful long-term stability using current devices. Metallic and graphite implants have been known to fatigue and will eventually fail if the desired solid bony fusion is not achieved. Thus, it would be advantageous to obtain successful bony fusion and spinal development while avoiding the use of devices having the aforementioned drawbacks.

SUMMARY OF THE INVENTION

The present invention is directed to resorbable interbody fusion devices for use as spacers in spinal fixation, wherein the device is composed of 25–100% bioresorbable or resorbable material. The devices can be in any convenient form, such as a wedge, screw or cage. In one embodiment, the interbody fusion device of the invention further desirably incorporates structural features such as serrations to better anchor the device in the adjoining vertebrae. In another embodiment, the device comprises a plurality of peripheral voids and more desirably a central void space therein, which may desirably be filled with a grafting material for facilitating bony development and/or spinal fusion, such as an autologous grafting material. In addition, void spaces increase the surface area of the device, thereby providing multiple sites for resorption to occur.

In yet another embodiment, the interbody fusion device of the invention further includes reinforcing fibers to enhance the structural properties thereof. These fibers may be made of the same polymeric material as the resorbable material from which the interbody fusion device is made, from a neutralization compound or, alternatively, from another biocompatible polymer, which may be crosslinked with a suitable crosslinking agent to yield an interpenetrating network for increased strength and stability. In another alternative embodiment, the reinforcing fibers are incorporated into the device, e.g., during the molding process, being placed in the mold under tension and released after the process of molding is complete.

Bioerodible polymers that are useful in the invention include polydioxanone, poly($\epsilon$-caprolactone); polyanhydride; poly(ortho ester); copoly(ether-ester); polyamide; polylactone; poly(propylene fumarate) ($H[-O-CH(CH_3)-CH_2-O-CO-CH=CH-CO-]_nOH$); and combinations thereof. In a preferred embodiment, the polymer poly(lactide-co-glycolide) (PLGA: $H[-OCHR-CO-]_nOH$, $R=H, CH_3$), with a lactide to glycolide ratio in the range of 0:100% to 100:0% inclusive, is used.

As many of the preferred bioerodible polymers from which the resorbable interbody fusion device is manufactured are polymers that can produce acidic products upon hydrolytic degradation, the device preferably further includes a neutralization compound, or buffer. The neutralization compound is included in sufficiently high concentration to decrease the rate of pH change as the device degrades, in order to prevent sterile abscess formation caused by the accumulation of unbuffered acidic products in the area of the implant. Most preferably, the buffering or neutralizing agent is selected from a group of compounds wherein the pKa of the conjugate acids of the buffering or neutralization compound is greater than the pKa of the acids produced by hydrolysis of the polymers from which the device is prepared.

The neutralization compound, or buffer, included in the bioerodible material of the invention may be any base, base-containing material or base-generating material that is capable of reacting with the acidic products generated upon hydrolysis of the bioerodible polymer. Polymeric buffers which preferably include basic groups which neutralize the acidic degradation products may also be used as buffering compounds. Another class of useful buffering compounds are those which, on exposure to water, hydrolyze to form a base as one reaction product.

In another alternative embodiment, the resorbable interbody fusion device of the invention preferably includes a biological growth factor, e.g., bone morphogenic protein, to enhance bone cell growth. To protect the growth factor and to provide for controlled delivery, the biological growth factor may itself be compounded with a resorbable polymer in some of the many techniques available and prepared as a growth factor/polymer composite in pellet form, in small particle form or within the interstices or pores of a polymeric foam or low-density polymer and this polymer/growth factor composite is deposited into void spaces of the resorbable spinal fusion device. Alternatively, the growth factor, or protected growth factor, may simply be directly incorporated into the component formulation of the resorbable spinal fusion device.

Active periosteum cells may also be incorporated into a foam, e.g., deposited into void spaces of the resorbable spinal fusion device, in order to facilitate bone cell fusion. Further, the resorbable spinal fusion device of the invention may be prepared in such a manner as to exhibit a piezoelectric effect, to enhance bone wound healing.

As used herein, the terms "resorbable" and "bioresorbable" are defined as the biologic elimination of the products of degradation by metabolism and/or excretion and the term "bioerodible" is defined as the susceptibility of a biomaterial to degradation over time, usually months. The terms "neutralization compound" or "buffer" are defined as any material that limits or moderates the rate of change of the pH in the implant and its near environment upon exposure to acid or base. The term "acidic products" is defined herein as any product that generates an aqueous solution with a pH less than 7.

DESCRIPTION OF THE DRAWINGS

The invention will be more fully understood from the following detailed description taken in conjunction with the accompanying drawings in which:

FIGS. 1A, 1B and 1C are perspective top, side and front views, respectively, of an interbody spinal fusion device according to the present invention;

DETAILED DESCRIPTION OF THE INVENTION

Figure 2A:
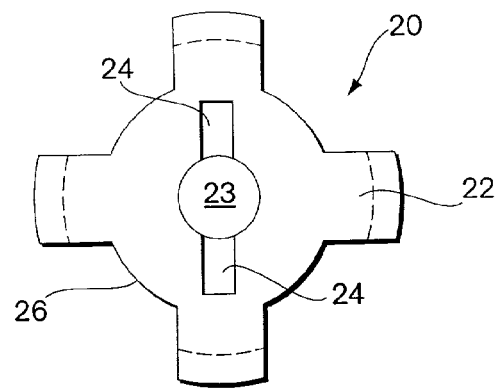
FIGS. 2A, 2B and 2C are top, side and perspective views, respectively, of another embodiment of an interbody spinal fusion device of the invention.

The present invention provides, in one embodiment, an interbody spinal fusion device (IFD) comprising a resorbable spinal wedge for vertebral spacing as an adjunct to spinal fusion. Made from a biodegradable, biocompatible polymer, preferably poly(lactic-co-glycolic) acid (PLGA), discussed further below, this resorbable spacer incorporates peripheral voids and central voids, which can be filled with autologous grafting material to facilitate bony development and spinal fusion, and serrated or threaded faces to stabilize and align vertebral bodies. The spinal fusion device of the invention is used as an adjunct to fusions of the cervical, thoracic or lumbar vertebrae, the configuration and dimensions of the device depending on the site of use.

A preferred embodiment of a spinal implant, fabricated from a biocompatible and biodegradable polyester and intended to replace a cervical disc, C4, 5, or 6, is shown in FIGS. 1A, 1B and 1C. A rod molded from a suitable material, as described below, is machined to the desired configuration and dimensions. Relatively complex geometries can be readily fabricated in this manner. Suitable biocompatible extraneous materials such as plasticizers or other machining aids, can be included in the material if desired.

As shown in FIG. 1A, a preferred resorbable interbody spinal fusion device of the invention 10 is in the shape of a tapered wedge, having a top face 11, a bottom face 12, side faces 13, a front end 14 and a back end 15. The surfaces of top and bottom faces 11 and 12 each have serrations 16 to aid in anchoring the device to the surrounding bone. Wedge 10 preferably contains holes 17 of convenient diameter, which may be drilled through the wedge to facilitate resorption of the polymer from which the device has been made. A plurality of channels or ports 18 through the wedge or a larger center hole 19 in the wedge are useful for the introduction of autologous bone. As illustrated in FIGS. 1B and 1C, the spinal wedge is preferably machined to have a taper from back end 15 to front end 14, such that the front end 14 is narrower than the back end 15.

Figure 2B:
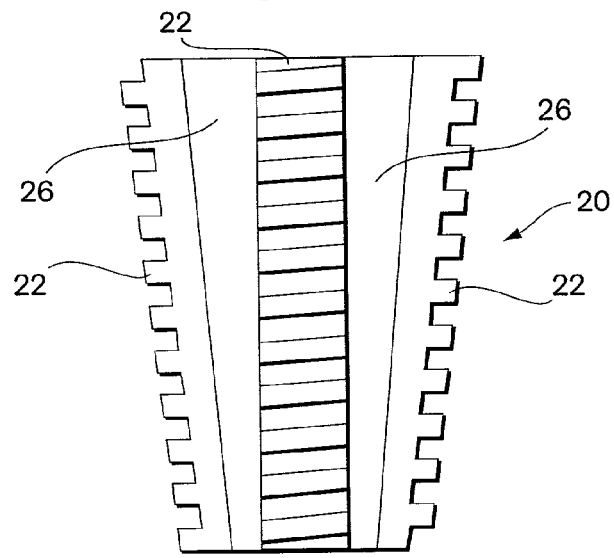
Figure 2C:
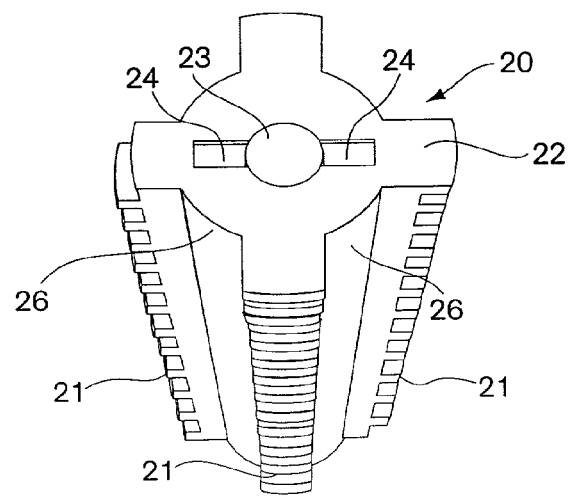

In another embodiment, as shown in FIGS. 2A–2C resorbable spinal fusion device 20 is shaped like a tapered rod having ridges 22 with threads 21. Device 20 functions as a screw and contains a cylindrical axially extending hole 23 and slots 24 to facilitate screwing the device into the spine of the patient. The device also contains recesses 26 between ridges 22 to facilitate ingrowth of tissue that would aid in anchoring the device in place.

Figure 3A:
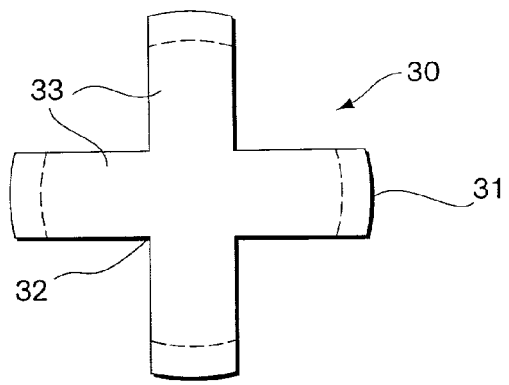
FIGS. 3A, 3B and 3C are top, side and perspective views, respectively, of another embodiment of an interbody spinal fusion device of the invention.
Figure 3B:
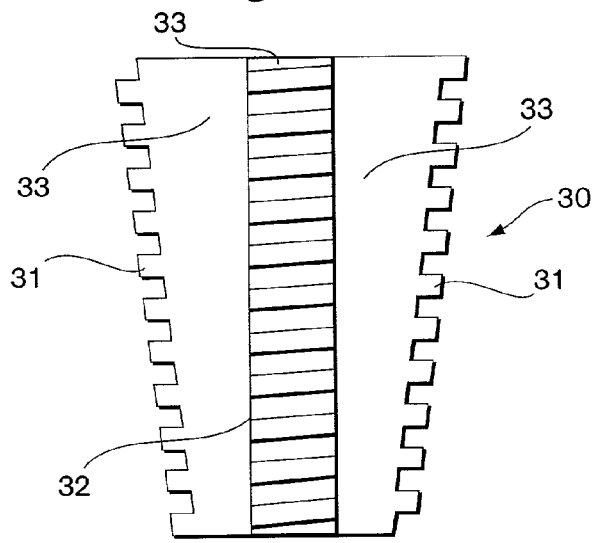
Figure 3C:
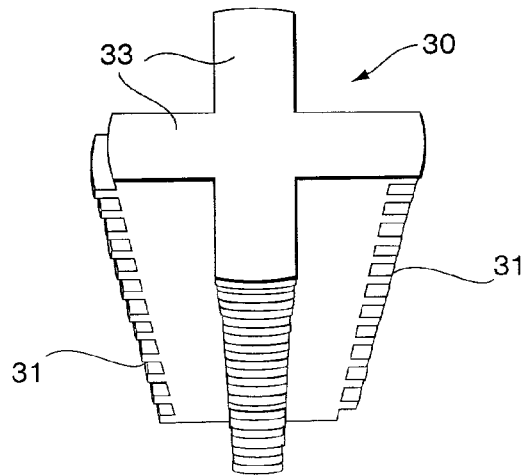
Figure 4A:
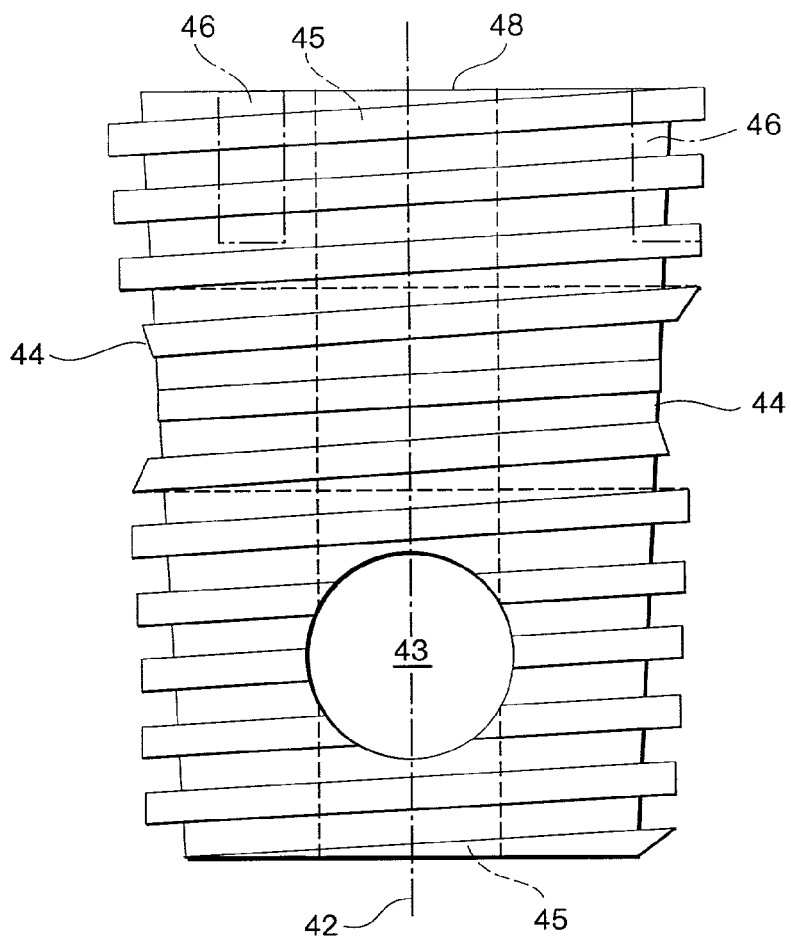
FIGS. 4A and 4B are side and top views, respectively, of another embodiment of an interbody spinal fusion device of the invention.
Figure 4B:
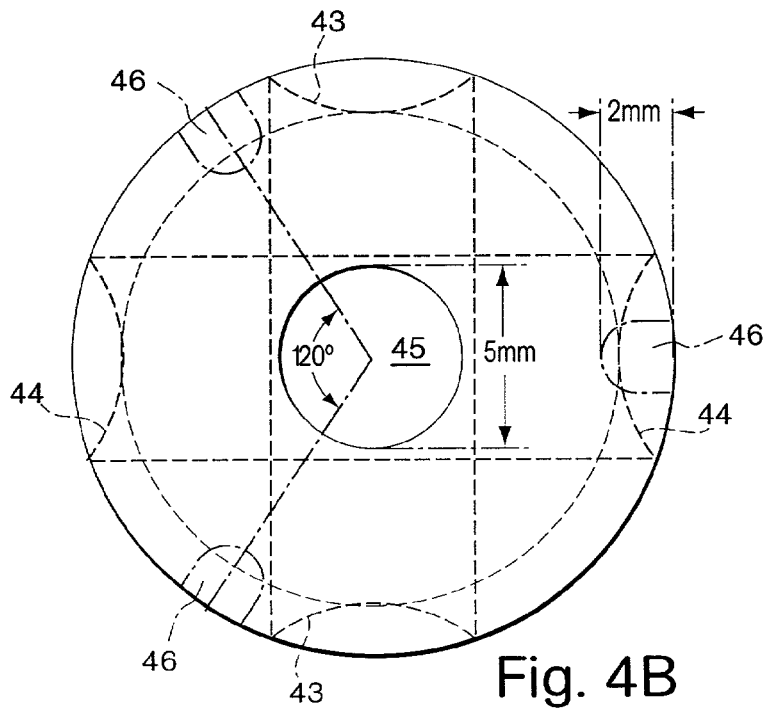

As shown in FIGS. 3A–3C, in a further embodiment, the device 30 is of cruciform shape having arms 33. Threads 31 extend the length of the outer surfaces of arms 33. In another embodiment, shown in FIGS. 4A–4B, the device is shaped like a threaded screw having a continuous thread 41 provided around the surface of the tapered body. Cylindrical holes 43 and 44 are provided through the body, the holes being orthogonal to each other and to screw axis 42. A cylindrical hole 45 is provided coaxially with axis 42. Slots 46 in the top 48 serve to position and retain a tool that can be used to screw the device into place.

Figure 5A:
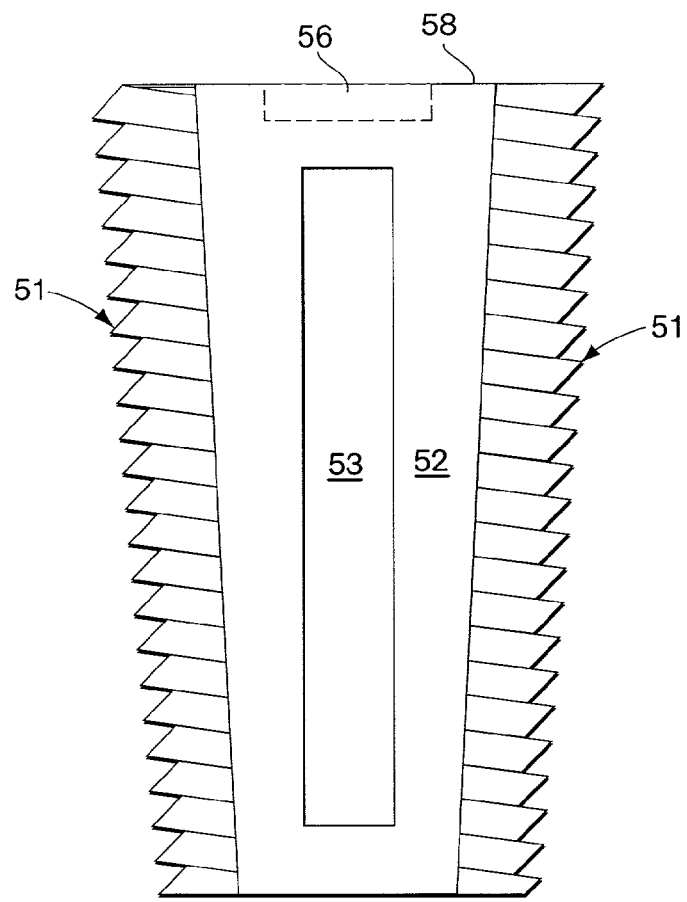
FIGS. 5A and 5B are side and top views, respectively, of another embodiment of an interbody spinal fusion device of the invention.
Figure 5B:
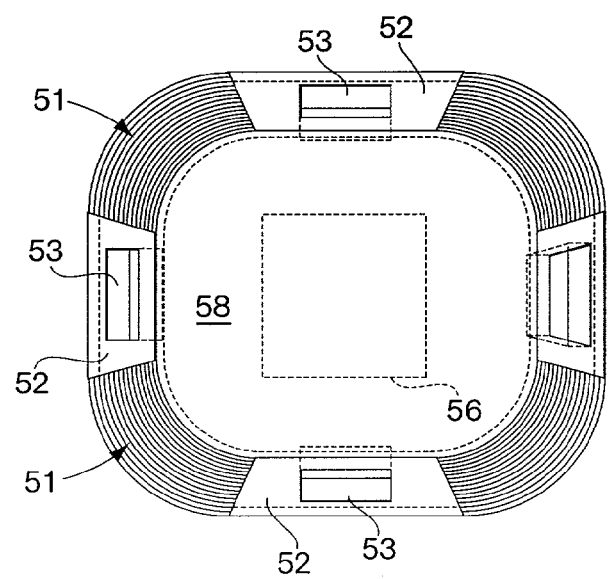

As shown in FIGS. 5A and 5B, a further embodiment of a threaded screw contains flat side areas 52 alternating with threaded corner areas 51. Slots 53 can be machined or otherwise provided in the flat areas, to facilitate ingrowth of tissue, and can be of a constant width or can be tapered. A slot 56 in top 58 of the device accommodates a suitable tool to facilitate insertion.

For replacement of one of the cervical discs C4, C5, or C6, the device shown in FIGS. 1A–1C preferably measures 15 mm laterally by 12 mm sagittally. The flattened side, positioned posterially, is 6–8 mm thick, enlarging to about 7–9 mm at the anterior edge; thus the device has a taper of approximately 4.8 degrees. Both surfaces are serrated, the serrations directed laterally. The serrations may be either square cut or cut at an angle with one face vertical and the other sloping upward anteriorly.

The thickness of the device of the invention will govern the rate at which it degrades and total degradation time. Thus, interbody spinal fusion devices can be prepared with multiple thicknesses, but all having the same approximately 5° taper. For example, the anterior thickness could range from 7 to 9 mm and the posterior thickness from 6 to 8 mm. The taper provides the correct orientation to the vertebrae with which the device is in contact and can also serve to keep the device in place.

The vertebral body is a fairly cylindrical mass consisting of cancellous bone surrounded by a thin layer of cortical bone. Thus, the mechanical properties of the device should preferably match those of the cancellous bone of the vertebrae in regard to proportional limit stress, compression at proportional limit, modulus of elasticity, failure stress and compression at failure (See, e.g., Lindahl, Acta Orthop. Scand. 47:11, 1976; Hansson et al., Spine 12:56, 1987).

Bioerodible polymers that are useful in the spinal fusion device of the invention include polydioxanone, poly(E-caprolactone); polyanhydride; poly(ortho ester); copoly (ether-ester); polyamide; polylactone; poly(propylene fumarate)(H[—O—CH(CH$_3$)—CH$_2$—O—CO—CH=CH—CO—]$_n$OH); poly(lactic acid); poly(glycolyic acid); poly (lactide-co-glycolide); and combinations thereof. Selection of a particular polymer is based primarily on the known properties of the polymer, such as the potentiality for cross-linking, polymer strength and moduli, rate of hydrolytic degradation, etc. One of ordinary skill in the art may take these and/or other properties into account in selecting a particular polymer for a particular application. Thus, the selection of a particular polymer is within the skills of the ordinary skilled practitioner.

In a preferred embodiment, the polymer poly(lactide-co-glycolide) (H[—OCHR—CO—]$_n$OH, R=H, CH$_3$) (PLGA) is used. The PLGA polymers used according to the invention desirably have a lactide to glycolide ratio in the range of 0:100% to 100:0%, inclusive, i.e., the PLGA polymer can consist of 100% L- or D,L-lactide (PLA), 100% glycolide (PGA), or any combination of lactide and glycolide residues. These polymers have the property of degrading hydrolytically in vivo to form organic acids (lactic acid and glycolic acid) which accumulate in the region surrounding the implant. These acids are metabolized and eventually excreted as carbon dioxide and water or enter the citric acid cycle.

The process by which alpha polyesters such as PLA, PGA, and PLGA biodegrade is primarily by non-specific hydrolytic scission of the ester bonds. The L-lactic acid that is generated when PLA or PLGA degrades becomes incorporated into the tricarboxylic acid cycle and is excreted from the lungs as carbon dioxide and water. Glycolic acid, produced both by random hydrolytic scission and by enzymatically mediated hydrolysis, may be excreted in the urine and also can enter the TCA cycle and eventually be oxidized to carbon dioxide and water (Hollinger et al., Clin. Orthop. Rel. Res. 207: 290–305, 1986).

A particularly preferred polymer for use in the device of the invention is poly(d,l-lactide-co-glycolide)-85:15 (Boehringer-Ingelheim: distributor, Henley Chemicals, Inc., Montvale, N.J.), the 85:15 designation referring to the lactide to glycolide mole ratio. The particularly preferred polymer is Resomer™ RG 858, with an inherent viscosity of approximately 1.4 corresponding to a weight average molecular weight of 232,000 as measured by gel permeation chromatography (GPC).

The polymer can be used as received or purified by precipitation from tetrahydrofuran solution into isopropanol, air dried and then exhaustively vacuum dried. Polymer data (composition and molecular weight) can be confirmed by nuclear magnetic resonance and by GPC (Hsu et al., J. Biomed. Mater. Res. 35:107–116, 1997).

Spinal fusions require interbody fusion devices that will maintain significant structural rigidity for 6–12 months. Strength requirements depend on the location of the disc to be replaced. When a person is standing, the forces to which a disc is subjected are much greater than the weight of the portion of the body above it. Nachemson et al. (Acta. Orthop. Scand. 37:177, 1966; J. Bone Joint Surgery 46:1077, 1964; Clin. Orthop. 45:107, 1966) has determined that the force on a lumbar disc in a sitting position is more than three times the weight of the trunk. Daniels et al. (J. Appl. Biomater. 1:57–78, 1990) have reviewed much of the mechanical data of PGA, PLA, and PLGA.

As a bioerodible polymer undergoes hydrolysis in the body, any acidic degradation products formed may be implicated in irritation, inflammation, and swelling (sterile abscess formation) in the treated area. To counteract this effect, a neutralization compound, or buffer, is desirably included in the bioerodible material to neutralize the acidic degradation products and thereby reduce the sterile abscess reaction, as described in copending U.S. application Ser. No. 08/626,521, filed Apr. 3, 1996, the whole of which is hereby incorporated by reference herein.

The buffering compound included in the bioerodible material of the invention may be any base, base-containing or base-generating material that is capable of reacting with the acidic products generated upon hydrolysis of the bioerodible polymer. Exemplary buffering materials include salts of inorganic or organic acids, salts of polymeric organic acids or polymeric bases such as polyamines. Preferably calcium salts of weak acids such as, e.g., tribasic calcium phosphate, dibasic calcium phosphate, or calcium carbonate are use. To be useful, the conjugate acids from which the buffering materials are derived must have a pKa greater than those of L-lactic acid (pKa=3.79), D, L-lactic acid (pKa=3.86), or glycolic acid (pKa=3.83), if a PLGA is the polymer which is undergoing hydrolysis. Thus, for example, salts of acetic acid (pKa=4.74), or succinic acid (pK$_1$=4.19, pK$_2$=5.64) may also be used.

Buffer compositions of lower solubility are preferred because buffer loss from the polymer by diffusion will be slower (Gresser and Sanderson, "Basis for Design of biodegradable Polymers for Sustained Release of Biologically Active Agents" in *Biopolymeric Controlled Release Systems*, Ch. 8, D. L. Wise, Ed., CRC Press, 1984). Preferably, the buffering compound has an acid dissociation constant that is smaller than the acid dissociation constant of the acidic products generated upon hydrolysis of the bioerodible polymer. Ionic buffers will, in general, be the salts of weak acids. The acid, of which the buffer is a salt, should have an ionization constant (acid dissociation constant, $K_a$) which is less than the $K_a$ for the acid products of polymer hydrolysis. Alternatively, the buffering compound has a hydrolysis constant that is greater than the hydrolysis constant of the acidic products.

Hydroxyapatite (HA) and calcium carbonate (CC) were each investigated as buffering fillers. Results demonstrate that the inclusion of CC or HA in a, e.g., PLGA fixture can effectively moderate the rate of pH decline as the fixture degrades. Further, the rapid decline in pH can be offset without considering 100% neutralization of the lactic and glycolic components. Thus, even given that the polymeric fixture will be filled with an inorganic buffer, the mechanical characteristics of the fixture can be stabilized since the loading requirements for the buffer will not be nearly as compromising as expected at the outset.

While both CC and HA can ameliorate the rate of decline in pH in the region of polymer hydrolysis, the use of hydroxyapatite as a filler also supports osteoconductivity. Thus, HA not only promotes bony ingrowth and obviates loosening of the fixture, but also acts as a buffer thereby preventing the formation of sterile abscesses that have been attributed to the acidic degradative products of PLGA implants. The resulting resorbable fixture should be capable of a buffered hydrolytic degradation and induction of bony ingrowth as resorption of the implant progresses. A resorbable buffered bone fixture with such properties could provide structural support to stabilize and support a spinal repair over the period of time required for natural healing to occur.

According to the invention a preferred buffering compound is hydroxyapatite. The formula $Ca_{10}(OH)_2(PO_4)_6$ may be written as $Ca(OH)_2 \cdot 3Ca_3(PO_4)_2$. When written in this manner it is seen that the following neutralization reactions may be written:

$$2RCO_2H + Ca(OH)_2 \cdot 3Ca_3(PO_4)_2 \rightarrow 2RCO_2^- + Ca^{+2} + 2H_2O + 3Ca_3(PO_4)_2$$

$$12RCO_2H + 3Ca_3(PO_4)_2 \rightarrow 6H_2PO_4^- + 9Ca^{+2} + 12RCO_2^-$$

The dissociation constant of water (the conjugate acid of the hydroxyl ion) is $K_w = 10^{-14}$. The basic phosphate ion, $PO_4^{-3}$, can neutralize two protons forming the following acids, for which dissociation constants are given:

$$RCO_2H + PO_4^{-3} \rightarrow RCO_2^- + HPO_4^{-2}$$

$$RCO_2H + HPO_4^{-2} \rightarrow RCO_2^- + H_2PO_4^-$$

$$K_2 \text{ of } H_2PO_4^{-1} = 6.2 \times 10^{-8}$$

$$K_3 \text{ of } HPO_4^{-2} 4.2 \times 10^{-13}$$

Buffers included in the polymer in solid form preferably have a relatively small particle size, for example, between less than 1.0 and 250 μm. Particle size reduction can be accomplished by any standard means known in the art, such as ball milling, hammer milling, air milling, etc. If buffer and polymer are to be blended by the dry mixing method (described below), the polymer particle size must also be considered. Polymers such as the PLGAs have relatively low glass transition temperatures and melting temperatures. Thus, polymer particle size reduction must be accompanied by cooling, for example using a Tekmar A-10 mill with a cryogenic attachment.

Following milling, the desired particle size range of the buffer and the polymer may be recovered by sieving through, for example, U.S. Standard sieves. Particles in the size ranges of <45, 45–90, 90–125, 125–180, 180–250 μm may be conveniently isolated.

In selection of particle size range, it is sometimes desirable to combine two or more ranges, or to use a wide range of sizes, for instance all sizes less than 250 μm. Larger particles may be preferred in some applications of the invention because larger particles take longer to be eroded by the acids and will therefore extend the useful lifetime of the buffer. In some cases particle size reduction will not be necessary, such as when commercially available precipitated calcium carbonate is used (e.g., Fisher Scientific, Inc., Catalog No. C-63).

The effectiveness of substances such as calcium carbonate and hydroxyapatite in neutralizing the acid products of polymer hydrolysis depends not only on the quantity of the substance in the matrix, but also on particle size and distribution, total surface area in contact with the polymer, and solubility.

Figure 8:
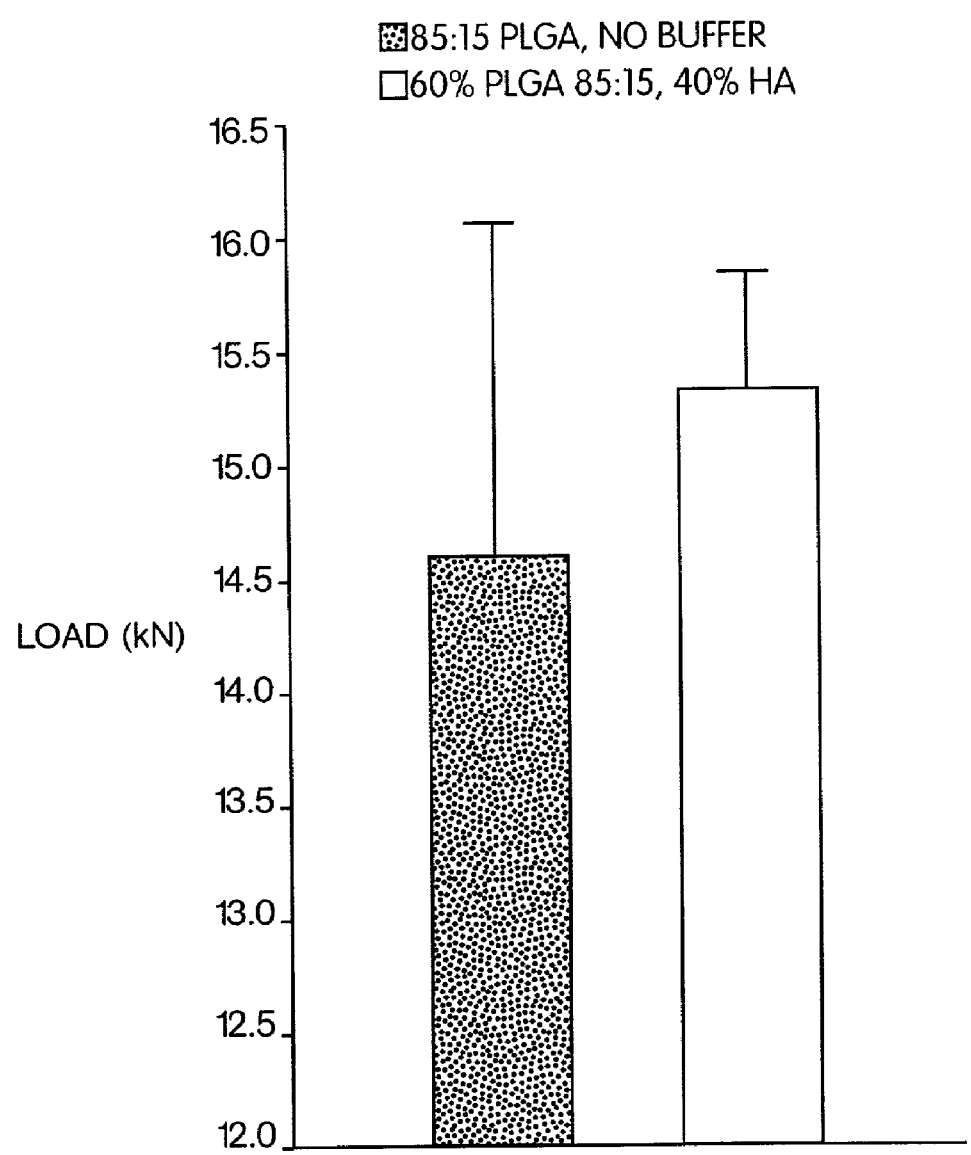
FIG. 8 shows compression strength with load for interbody spinal fusion devices of the invention with and without the incorporation of a buffering or neutralizing compound.

The presence of calcium ions in the buffered device has advantages with respect to the physical properties of the device as it undergoes erosion. It has been shown that calcium ions form ionic bridges between carboxylate terminal polymer chains (Domb et al., J. Polymer Sci. A28, 973–985 (1990); U.S. Pat. No. 4,888,413 to Domb). Calcium ion bridges between carboxylate anions increase the strength of the composite in which the polymer chains are terminated by carboxylate anion end groups over similar chains terminated by the hydroxyl groups of, e.g., terminal glycol moieties or terminal a-hydroxy acids. In an analogous manner, the polyesters comprising the family of PLGA's are expected to be strengthened by calcium bridges between carboxylate anion terminated chains. As shown in FIG. 8 PLGA-85:15 wedges reinforced with 40% HA showed an increase in compressive strength of approximately 5% over the nonreinforced controls.

Another class of useful buffering compounds are those which, on exposure to water, hydrolyze to form a base as one reaction product. The generated base is free to neutralize the acidic products produced upon hydrolysis of the bioerodible polymer. Compounds of this type include aryl or alkyl carbamic acids and imines. These "basegenerating compounds" offer the advantage that the rate of hydrolysis of the base generator may be selected to correlate to the rate of hydrolysis of the bioerodible polymer.

Necessarily, the conjugate acid of the buffering compound has an acid dissociation constant that is smaller than the acid dissociation constant of the acidic products generated upon hydrolysis of the bioerodible polymer. Alternatively, the buffering compound preferably has a hydrolysis constant that is greater than the hydrolysis constant of the acidic products.

Furthermore, the buffering compound preferably is only partially soluble in an aqueous medium. In general, buffers of lower solubility are preferred because buffer loss from the polymer by diffusion will be minimized (Gresser and Sanderson, supra). The quantity of buffer to include depends on the extent of neutralization desired. This may be calculated as shown below, using a PLGA of any composition buffered with calcium carbonate as an example.

The average residue molecular weight, RMW, for a PLGA is given by $$RMW = 14.03x + 58.04$$

where x=mole fraction of lactide in the PLGA. The term "residue" refers to the repeating lactide or glycolide moiety of the polymer. For example, if x=0.85 (PLGA=85:15), RMW=69.96. Thus, 1.0 gram of PLGA=85:15 contains 0.01429 moles of residues which, on hydrolysis of the polymer, will yield 0.01429 moles of lactic and/or glycolic acid. If, e.g., calcium carbonate is the buffering agent, and it is desired to neutralize, e.g., 50 mole % of the acids by the reaction $$CaCO_3 + 2HA \rightarrow CaA_2 + H_2O + CO_2$$

where A=lactate or glycolate, then the weight of calcium carbonate needed is (0.25) (0.01429) (100.09)=0.358 gram, and the required loading is (0.358) (1+0.358) (100)=26.3% by weight.

Several methods may be used to incorporate the buffer into the polymer. These methods include solution casting coupled with solvent evaporation, dry mixing, incorporating the buffer into a polymer foam, and the polymer melt method.

Solution casting coupled with solvent evaporation may be used with buffers which are either soluble or insoluble in the solvent. The bioerodible polymer is dissolved in any suitable volatile solvent, such as acetone, tetrahydrofuran (THF), or methylene chloride. The buffer, which may be soluble or insoluble in this solvent, is added to give the final desired ratio of polymer to buffer. If particle size reduction of the buffer is necessary, it may be accomplished by ball milling the suspension of buffer in the polymer solution. In contrast, if the buffer is soluble in the chosen solvent, particle size reduction at any stage is not necessary.

The suspension or co-solution is cast as a film on a glass or other inert surface, and the solvent is removed by air drying. Residual solvent remaining in the film may be further removed by subjecting the film to vacuum drying at elevated temperatures. As an example, if calcium carbonate is to be used as a buffering compound and it is desired to neutralize 50% of the acid formed by hydrolysis of PLGA-50:50, the buffer content of the composition should be 27.8%.

In an exemplary embodiment, to prepare 50 grams of composite, 36.1 grams of PLGA-50:50 are dissolved in approximately 250 ml of tetrahydrofuran, and 13.9 grams of calcium carbonate of the desired particle size range is added to the solution mixture. After distributing the calcium carbonate homogeneously by mixing, the suspension is dried to a film as described above.

The resulting film may be processed by compaction under high pressure, extruded through a die, injection molded, or other method known in the art. Further definition of the final shape may be accomplished at this point by any desirable machining process, such as lathing.

In the dry-mixing method, a polymer of appropriate particle size range is mixed with the buffer, also of chosen particle size range, in proportions to give the desired stoichiometric buffering capacity. The dry mixture is thoroughly blended by rotating the mixture in a ball mill jar from which the grinding balls have been omitted, or other suitable mixing device. The blended mixture may then be processed by compaction, extrusion, injection molding, etc., as described above.

In the polymer melt method, a known weight of the buffer is incorporated by mixing into a known weight of a suitable melted polymer. A quantity of polymer is heated to a temperature above its melting point, and a suitable buffer is blended into the melted polymer. The resulting polymer/buffer composite is solidified by cooling, and may be processed as described above, or ground and sieved prior to processing.

In some applications, it may be desirable to protect the buffering compound, for example, during processing according to the melt method, or to make the buffering compound available at the later stages of polymer degradation. In such cases, it is desirable to coat the buffering compound particles with a material that degrades at a slower rate than the material chosen for the fixation devices. Thus, the buffering compound is exposed only after the body of the device and the coating material have partially degraded.

Exemplary materials used to coat the buffering compound particles include high molecular weight poly(L-lactide) or poly(ε-caprolactone).

The particles of buffering compound may be coated with the protective material by any method that coats particles, such as spray coating with a solution of protecting polymer or micro-encapsulation. Alternatively, a chosen protective polymer may be made in a melted state and buffer particles are added. The melt is cooled and ground and milled to the desired particle size range. Alternatively, the buffering compound may be added to a solution of the protective polymer and removing the solvent by evaporation. The dried mass is compacted in a mold under high pressure and grinding or milling the compacted mass to the appropriate particle size range.

The resorbable spinal fusion device of the invention optionally includes a biological growth factor, e.g., bone morphogenic protein, to enhance bone cell growth. To protect the growth factor and to provide for controlled delivery, the biological growth factor may be itself compounded with a resorbable polymer by one of the many techniques available and prepared as a growth factor/polymer composite in pellet form, in small particle form or within the interstices or pores of a polymeric foam or low-density polymer and this polymer/growth factor composite deposited into void spaces of the resorbable spinal fusion device. Alternatively, the growth factor may simply be directly incorporated into the component formulation of the resorbable spinal fusion device.

Active periosteum cells, or other bony cells, may be also incorporated into a foam surrounding, or deposited in, the resorbable spinal fusion device so that the cells may facilitate bone cell fusion. To carry out such an incorporation, the periosteum surrounding a human bone is removed and cultured following standard cell culturing techniques. The scaffold for such periosteum cell growth is a resorbable polymer foam or mesh. This scaffolding is prepared by dipping the completed device in a polymer/solvent (such as PLGA dissolved in acetic acid). The so-wetted device is then frozen and subsequently freeze-dried (lyophilized) resulting in a foam layer (or coating) of polymer surrounding the device. After the periosteum cells have been grown in this foam layer, the device is incorporated into the spine for the enhancement of spinal fusion.

In another embodiment, the resorbable spinal fusion device may be prepared in such a manner as to exhibit a piezoelectric effect. It is known that oriented (molecularly aligned) biopolymers such as PLGA have piezoelectric characteristics. In addition, the oriented biopolymer poly-l-lactic acid (PLLA) has been shown to promote bone wound healing (Shimono et al., In Vivo 10:471–476, 1996 and Ikada et al., J. Biomed, Mater. Res. 30:553–558, 1996). To take advantage of this phenomenon, the resorbable polymer is first aligned, by drawing, for example, such that all polymer chains are essentially parallel. The spinal fusion device is then cut from this aligned polymeric material such that the polymer chains are at approximately a 45° angle to the surface of the device, this angle being known to produce the optimal piezoelectric effect. Buffers, reinforcement materials, growth factors, etc., may also be included in processing of the spinal fusion device to exhibit this phenomenon.

As described by White et al. (Clinical Biomechanics of the Spine, 2nd edition, 1990), there are four stages of maturation of the arthrodesis (spinal fusion): I, fibrous healing; II, mixed fibrous and osseous healing; III, immature osseous healing; and IV mature osseous healing. Stage I requires maximum protection with restricted activity and perhaps a protective orthosis. During stage II relatively less protection is required although with restricted activity. During stage III the patient is allowed normal but nonvigorous activity. In stage IV, maximum healing will be reached. For clinically stable patients the first three stages require about six weeks each, and stage IV, a minimum of six weeks. Clinically unstable patients require more time, especially for the first two stages. Thus the goals for duration and strength may be estimated.

A prototype device has been prepared for in vitro determination of weight loss and failure strength as a function of time. Due to the asymmetric design of the IFD, it is not feasible to measure the compressive modulus over time of the in vitro prototypes. This parameter, as well as failure and ultimate strength over time in vitro, has been measured on cylindrical discs of the same overall dimensions. In vitro experiments permit monitoring of the change in molecular weight in time for correlation with the mechanical measurements. Devices are tested for mechanical properties, e.g., compressive strength, compressive modulus, with equipment such as, e.g., the TA-XT2 Texture Analyzer (Texture Technologies Corporation) or the Instron 8511 Servo-Hydraulic System (Instrom Corp.).

PLGA-85:15 (Resomer RG 858) including reinforcing fibers and HA buffer was molded at approximately 50° C. under a force of 7–9 tons to form a translucent cylindrical rod 1.6 cm in diameter and 5.0 cm in length. Devices were then machined to the appropriate final dimensions, as discussed earlier. White and Panjabi (p. 29) report dimensions and stresses to which thoracic vertebrae are subject. The average area of the upper and lower end plates of T1 is about 340 mm$^2$, and is subject to a loading force of about 2000 N. The compressive strengths of exemplary buffered and reinforced devices were, in all cases, greater than 13,000 N. Thus, the initial strength of these PLGA-85:15 devices is in excess of the stress to which cervical vertebrae will be subject and greater also than clinical targets of 10,000 N. Devices so made do not fracture at failure but rather irreversibly compress.

Figure 7:
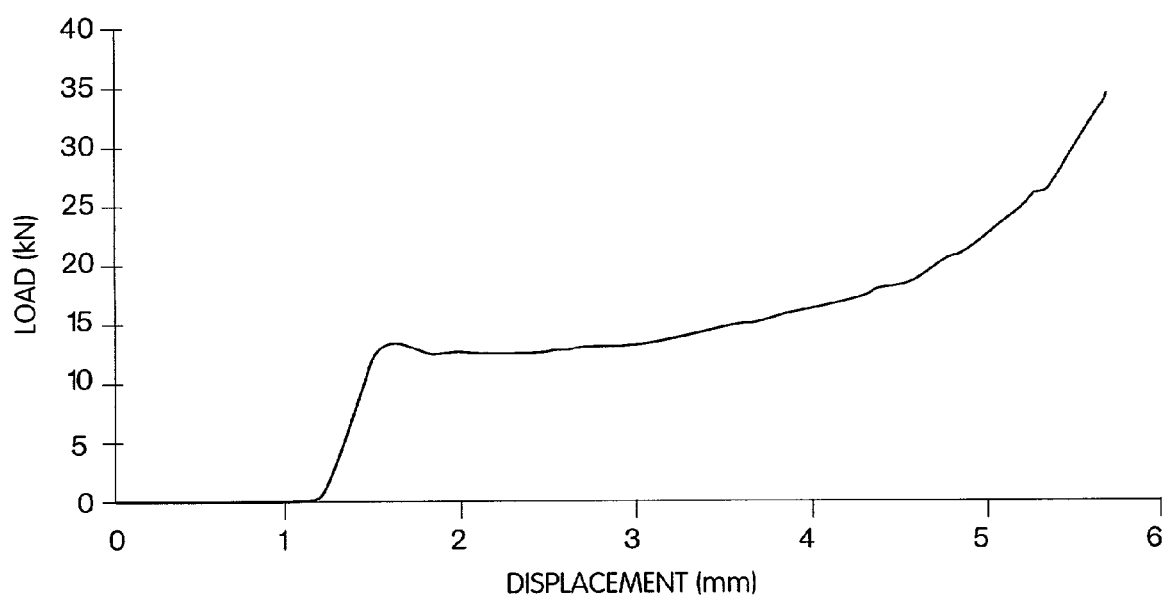
FIG. 7 is a plot of displacement versus load for an interbody spinal fusion device of the invention.

FIG. 7 illustrates this phenomenon. Failure at 13 kN is indicated by a slowly rising load at displacements greater than about 1.5 mm. If the tested device had failed by fracture, a rapid drop in load would have resulted. The design of the IFD and the PLGA comonomer ratio (i.e., lactide:glycolide ratio) enable the device to function through the four stages of healing with progressive loss of mass and strength. In clinically stable situations, at the end of stage I, the device should retain 70–80% of its mechanical strength, and at the end of stage II, 50% of its strength should be retained. During stages III and IV, further slow degradation will occur with complete resorption by one year.

Prototype devices have been prepared for feasibility trials with goats as the animal model. A viable model for testing fusion materials in the cervical spine is the in vivo goat model. Unlike most quadrupeds, the goat holds its head erect, thus loading the cervical vertebrae in a manner similar to humans. Although there are geometric differences, the relative sizes of the disc and vertebral bodies are similar to those of the human. (Pintar et al., Spine 19:2524–2528, 1994; Zdeblick et al., Spine 17(105):5418–5426, 1992.) The goat is thus the animal model of choice for testing the spinal fusion device of the invention.

The experimental procedure followed in the in vivo goat model is as follows. Anesthetized animals undergo implantation via a surgery to the anterior cervical spine (Pintar et al., Spine 19:2524–2528, 1994). After exposing the lower cervical segments, discectomy is performed at four levels. Two resorbable IFD's filled with cancellous bone are placed in two of these spaces, the others receive a piece of tricortical iliac bone graft in place. The bone graft and cancellous bone are harvested from the goat iliac crest through a separate incision over the hip bone. Placement of the IFD or the graft in upper or lower sites is alternated for each animal with an intact disc space between implants. The operative sites are closed, and the animals allowed to recover.

At sacrifice, the spinal column of the goat is excised leaving the intact ligamentous column. The cervical and lumbar sites are separated and radiographed before mounting for biomechanical (as described above) or histological analyses for resorptive activity and new bone formation. The fusion rate and biomechanical stiffness are evaluated for spinal units harvested from the goats. Spinal units undergo radiographic imaging to assess fusion, biomechanical testing to assess strength, and histological analysis to assess tissue changes. The results are compared to conventional graft-based spacers and fusion devices.

PLGA implants can be effectively reinforced by the use of degradable scaffolds which are molecularly dispersed in the host PLGA polymer. For example, a solid solution containing PLGA, poly(propylene fumarate) (PPF), and vinyl pyrrolidinone(VP) as a crosslinking agent (or other vinyl monomer) may be heated with an initiator (such as benzoyl peroxide). The PPF chains are crosslinked by VP to form an interpenetrating network of crosslinked PPF and PLGA polymer chains. Following heating, further crosslinking is possible using y-irradiation, e.g. 2.5 mrad.

Several reinforcement techniques described in the literature include self-reinforcement using aligned PLGA fibers (Vainionpaa et al., Biomaterial 8:46–48, 1987; Pihlajamaki et al., J. Bone and Joint Surgery 74:13:853–857, 1992; Ashammakhi et al., J. Biomedical Materials Research 29: 687–694, 1995) and reinforcement with calcium phosphate glass fibers (R. A. Casper et al., Polym. Mater. Sci. Eng. 53:497–501, 1985).

Figure 6A:
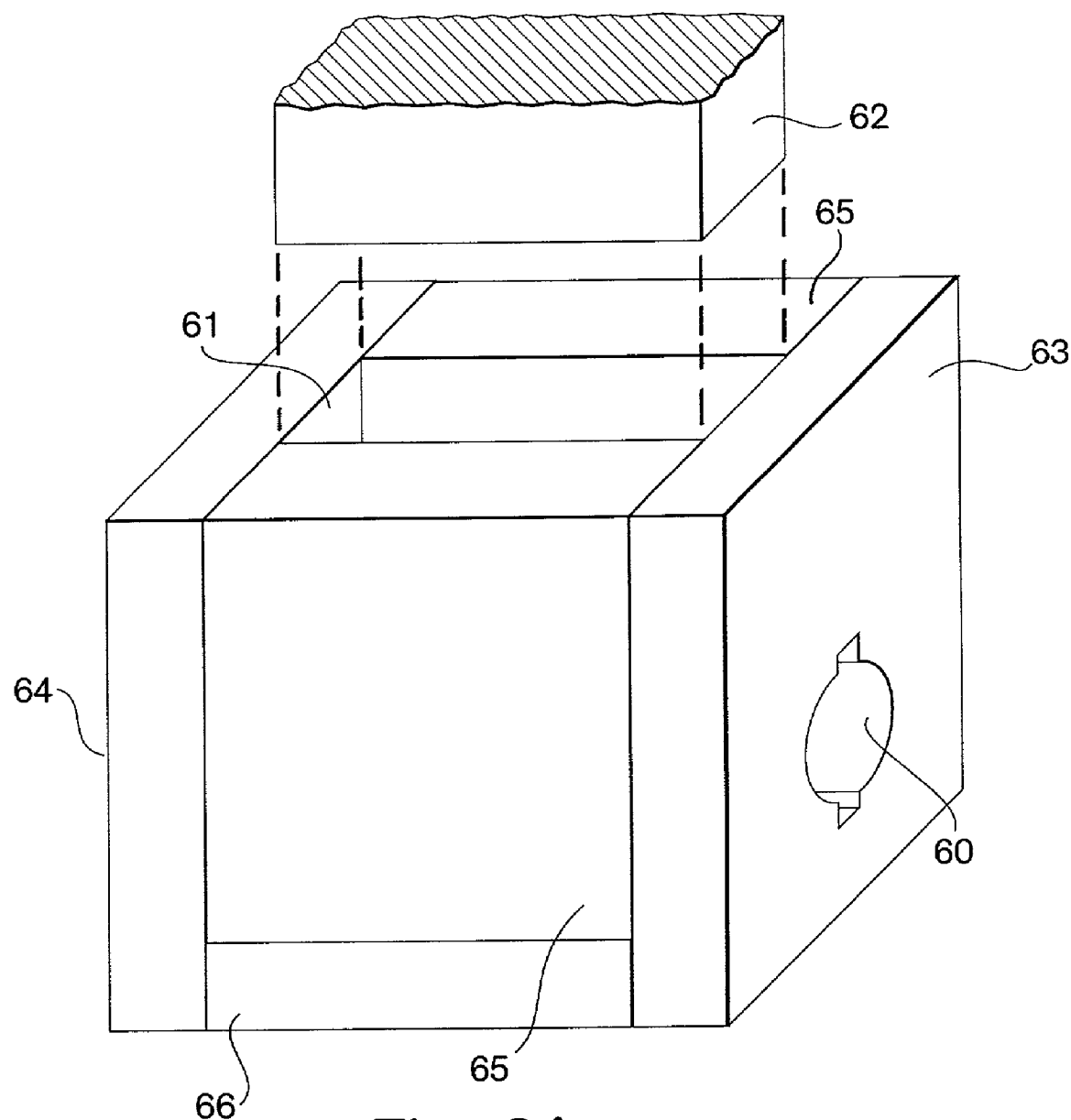
FIG. 6A is a perspective view of a mold and ram assembly for preparing an interbody spinal fusion device of the invention.

Reinforcement can also be achieved according to the invention by molding a rod of rectangular or other suitable cross-section that contains fibers under tension using the mold and ram assembly of the invention, as shown in FIGS. 6A–6G. Referring to FIG. 6A, mold cavity 61 and ram 62 are rectangular in cross-section in the illustrated embodiment. The mold illustrated is constructed of five plates (front face plate 63, rear face plate 64, side plates 65 and bottom plate 66), suitably fastened or bonded together. The front and rear face plates 63, 64 are machined or otherwise formatted, as will be described below, with key holes 60 to receive holder assemblies for the reinforcing fibers, which comprise front and rear tension tubes, front and rear tension tube caps, serrated discs, and a front tension tube threaded nut.

Figure 6B:
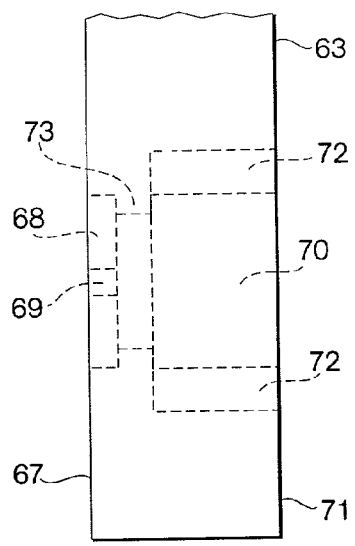
FIGS. 6B and 6C are edge and plan views, respectively, of the front face plate of the mold of FIG. 6A.
Figure 6C:
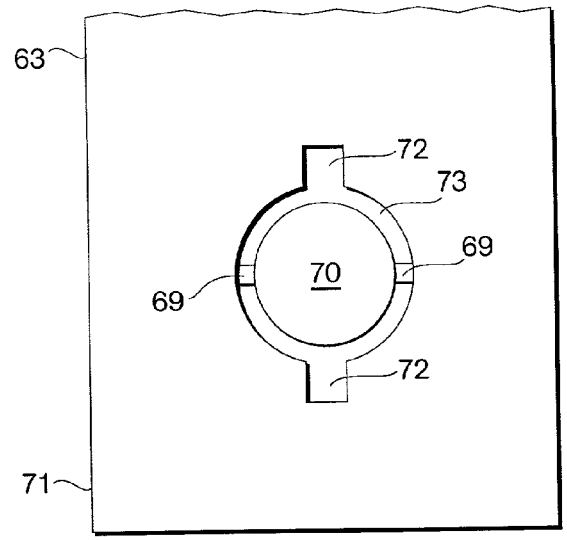
Figure 6D:
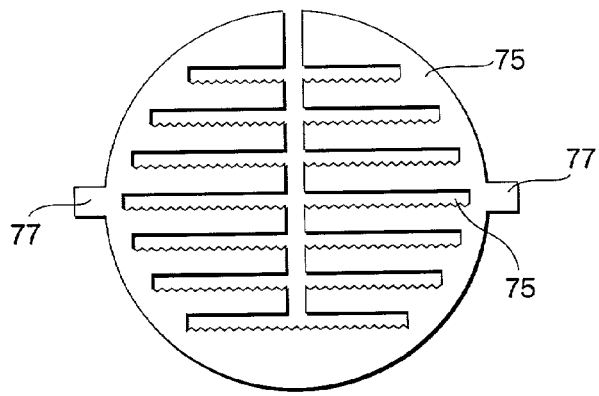
FIG. 6D shows a disc with serrated slots for use in the mold of FIG. 6A.
Figure 6E:
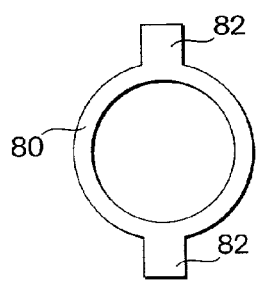
FIGS. 6E and 6F are front and side views, respectively, of a threaded tension tube used with the mold of FIG. 6A.
Figure 6F:
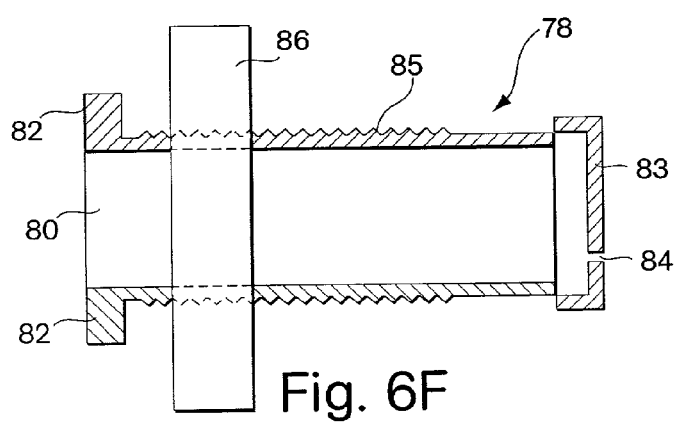

Referring to FIG. 6B (an edge view of front face plate 63) and FIG. 6C (a plan view of front face plate 63), the inside face 67 of plate 63 contains a circular recess 68, with associated slots 69. Recess 68 adjoins a larger recess 70 that extends to the outside face 71 of front face plate 63. Recess 70 includes associated slots 72. The axis between slots 72 is perpendicular to the axis between slots 69. A smaller diameter recess stop 73 separates recess 68 from recess 70. Rear face plate 64 is similarly configured.

Figure 6G:
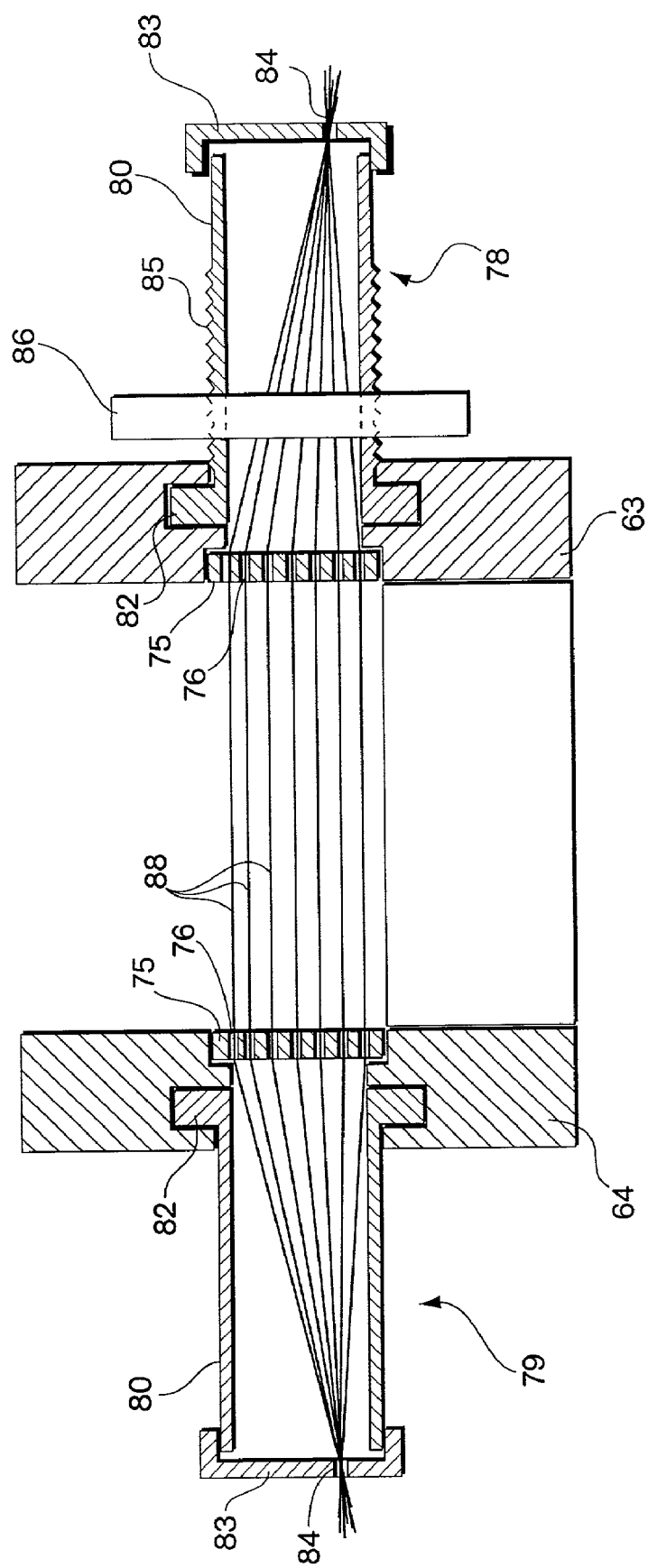
FIG. 6G is a section through a mold assembly fitted with reinforcing fibers and associated holder assemblies.

Referring now also to FIGS. 6D–G, the mold is assembled for use as follows. A disc 75 (FIG. 6D) having serrated slots 76 is threaded with polymer fibers 88, which are distributed throughout the serrated slots. The distribution of the fibers is spatially maintained by the serrations. Referring also to FIG. 6G, discs 75 with fibers in place are mounted in recesses 68 in the front and rear face plates 63, 64 of the assembled mold. Orientation of discs 75 is maintained by vanes 77 on the sides of the discs, which fit into slots 69. Alternatively, discs 75 may be mounted first in face plates 63, 64 and threaded in place. The protruding fiber bundles are then threaded through front and rear tension tube assemblies 78, 79, which are positioned in recesses 70 in the front and rear face plates 63, 64, respectively. Tension tube assemblies 78, 79 consist of tension tubes 80, each having vanes 82 which fit into slots 72 in the front and rear face plate recesses 70, respectively, thus maintaining the orientation of the tubes. The tension tubes are closed with caps 83 to complete assemblies 78, 79. The fiber bundles are threaded additionally through holes 84 in the front and rear tension tube caps, as they exit the tension tubes. Holes 84 are off-center and below the axis of the tension tubes. This configuration holds the fibers against the serrations of the discs. Outside the caps, the fibers may be knotted to keep them from slipping back through the holes. Other methods of anchoring the fibers may be used. For example, a bead of cement (such as epoxy or cyanoacrylate adhesives) may be built up on the outside of the caps to keep the fibers from slipping through. Also referring to FIGS. 6E and 6F, it can be seen that the tension tube 80 of front tension tube assembly 78 is exteriorly threaded 85 along its length and equipped with a nut 86 which, when tightened against the face plate, pulls the tension tube partially out of the face plate, thus putting the fibers under tension.

To prepare a reinforced resorbable spinal fusion device, mold cavity 61 of the assembled mold is then filled with the appropriate powdered formulation. The powdered formulation may be evenly distributed among the fibers by placing the mold on a vibrator. Ram 62 is put in place, in the opening of the mold, and pressure is exerted. The mold may be heated externally with heating tapes, or it may be so machined as to have recesses for cartridge heaters. When the molding process is complete, the tension on the reinforcing fibers is released, and the completed device is removed from the mold.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A resorbable interbody spinal fusion device for spinal fixation, said device comprising an interbody spinal fusion device comprising
   (1) between 25 and 100% of a biocompatible, bioerodible polymer which produces acidic products or low molecular weight resorbable fragments upon hydrolytic degradation, wherein the polymer includes a strengthening material selected from the group consisting of crosslinked monomers, reinforcing fibers, self-reinforcing aligned fibers of the polymer, degradable polymeric scaffolds, and interpenetrating networks,
   (2) one or more void spaces, and
   (3) a buffering or neutralizing agent,
   wherein one or more of the void spaces comprises a grafting material for facilitating bony development or spinal fusion.

2. The resorbable interbody spinal fusion device of claim 1, wherein said grafting material is an autologous grafting material.

3. The resorbable interbody spinal fusion device of claim 1, wherein said device is shaped substantially as a tapered wedge or cone.

4. The resorbable interbody spinal fusion device of claim 1, wherein said device is shaped substantially as a threaded screw.

5. The resorbable interbody spinal fusion device of claim 1, wherein said device is shaped substantially as a threaded rod of cruciform configuration.

6. The resorbable interbody spinal fusion device of claim 3, the device further comprising at least one serrated or threaded outer face.

7. The resorbable interbody spinal fusion device of claim 1, wherein said polymer or strengthening material is selected from the group consisting of polydioxanone, poly($\epsilon$-caprolactone), polyanhydride, polyester, copoly(ether-ester), polyamide, polylactone, poly(propylene fumarate), and combinations thereof.

8. The resorbable interbody spinal fusion device of claim 7, wherein said bioerodible polymer is poly(lactide-co-glycolide) with a lactide to glycolide ratio in the range of 0:100% to 100:0% inclusive.

9. The resorbable interbody spinal fusion device of claim 1, wherein said buffering or neutralizing agent is a polymer comprising at least one basic group.

10. The resorbable interbody spinal fusion device of claim 9, wherein the basic group is selected from the group consisting of polyamines, polyesters, vinyl polymers, and copolymers of acrylic acid.

11. The resorbable interbody spinal fusion device of claim 1, wherein said buffering or neutralizing agent is a compound that, on exposure to water, hydrolyzes to form a base.

12. The resorbable interbody spinal fusion device of claim 1, wherein said buffering or neutralizing agent is selected from the group consisting of carbonates, phosphates, acetates, succinates and citrates.

13. The resorbable interbody spinal fusion device of claim 1 wherein said strengthening material includes reinforcing fibers.

14. The resorbable interbody spinal fusion device of claim 13, wherein said reinforcing fibers are made of said a bioerodible polymer.

15. The resorbable interbody spinal fusion device of claim 13, wherein said reinforcing fibers are made of said buffering or neutralizing agent.

16. The resorbable interbody spinal fusion device of claim 1, wherein said buffering or neutralizing agent is selected from the group consisting of compounds wherein the pKa of the conjugate acids of said compounds is greater than the pKa of acids produced by hydrolysis of the polymer.

17. The resorbable interbody spinal fusion device of claim 1, wherein said device is fabricated from at least two bioerodible polymers.

18. The resorbable interbody spinal fusion device of claim 17, wherein one of said polymers is poly (propylene fumarate) which acts as a reinforcing material.

19. The resorbable interbody spinal fusion device of claim 17, wherein one of said polymers has been cross-linked in the presence of a crosslinking agent and an initiator, whereby said crosslinked polymer forms a reinforcing interpenetrating network.

20. The resorbable interbody spinal fusion device of claim 17, wherein one of said at least two polymers has been cross-linked in the presence of vinyl pyrrolidone as a crosslinking agent and an initiator.

21. The resorbable interbody spinal fusion device of claim 17, wherein one of said at least two polymers has been cross-linked in the presence of a crosslinking agent and benzoyl peroxide as an initiator.

22. The resorbable interbody spinal fusion device of claim 1, wherein said device is fabricated from a polymer wherein molecular chains of said polymer have been aligned to be essentially parallel.

23. The resorbable interbody spinal fusion device of claim 22, wherein said device lass been cut such that the aligned polymer molecular chains are at approximately a 45° angle to a surface of said device.

24. The resorbable interbody spinal fusion device for spinal fixation of claim 1, wherein said buffering or neutralizing agent is hydroxyapatite.

* * * * *